United States Patent
Goto et al.

(10) Patent No.: US 6,712,817 B1
(45) Date of Patent: Mar. 30, 2004

(54) TREATMENT INSTRUMENT FOR ENDOSCOPE

(75) Inventors: Hiroaki Goto, Hachioji (JP); Akihito Sadamasa, Hachioji (JP)

(73) Assignee: Olympus Optical Co., Ltd., Tokyo (JP)

( * ) Notice: Subject to any disclaimer, the term of this patent is extended or adjusted under 35 U.S.C. 154(b) by 0 days.

(21) Appl. No.: 09/499,546

(22) Filed: Feb. 7, 2000

(30) Foreign Application Priority Data

Feb. 25, 1999 (JP) .......................................... 11-048041

(51) Int. Cl.⁷ .............................................. A61B 18/18
(52) U.S. Cl. ...................................................... 606/47
(58) Field of Search ............................. 606/27, 28, 29, 606/31, 37, 39, 41, 45, 113, 170, 46, 47, 167

(56) References Cited

U.S. PATENT DOCUMENTS

| 4,181,131 | A | * | 1/1980 | Ogiu .............................. 606/47 |
| 4,325,374 | A | * | 4/1982 | Komiya ......................... 606/47 |
| 4,485,812 | A | * | 12/1984 | Harada et al. ......... 128/303.15 |
| 4,718,419 | A | * | 1/1988 | Okada .......................... 606/47 |
| 4,846,175 | A | * | 7/1989 | Frimberger .................. 606/47 |
| 5,078,716 | A | * | 1/1992 | Doll .............................. 606/47 |
| 5,437,665 | A | * | 8/1995 | Munro .......................... 606/47 |
| 5,810,807 | A | * | 9/1998 | Ganz et al. .................... 606/47 |
| 5,984,920 | A | * | 11/1999 | Steinbach ..................... 606/47 |
| 6,312,429 | B1 | * | 11/2001 | Burbank et al. ............... 606/47 |

FOREIGN PATENT DOCUMENTS

| JP | 58-152912 | 10/1983 |
| JP | 4-307055 | 10/1992 |
| JP | 5-176940 | 7/1993 |

* cited by examiner

Primary Examiner—Corrine McDermott
Assistant Examiner—Alvin Stewart
(74) Attorney, Agent, or Firm—Frishauf, Holtz, Goodman & Chick, P.C.

(57) ABSTRACT

A treatment instrument for an endoscope includes a main body, a cutting wire and an insertion portion. The cutting wire has an insertion portion inserted in the main body and an exposed portion situated at a distal side of the insertion portion and exposed out of the main body. The cutting wire is supplied with high-frequency current, and the insulating member electrically insulates a peripheral surface of the cutting wire. The insulating member insulates that part of the exposed portion, which is other than a non-insulated portion extending in a range of 5 mm to 15 mm from a distal end of the exposed portion. The excision portion is formed of the non-insulated portion of the cutting wire.

16 Claims, 4 Drawing Sheets

TREATMENT INSTRUMENT FOR ENDOSCOPE

RELATED APPLICATIONS

This application claims priority of foreign document JP-11-048041, filed Feb. 25, 1999.

BACKGROUND OF THE INVENTION

The present invention relates to a treatment instrument for an endoscope (hereinafter referred to as "endoscopic treatment instrument"), which is inserted into the body via a treatment instrument insertion channel in the endoscope to perform high-frequency excision of an affected part.

There is a generally known example of an endoscopic treatment instrument to be inserted into the body via a treatment instrument insertion channel in an endoscope, which comprises an insertion section formed of a long, flexible tube, etc., and an electrically conductive cutting wire exposed to a distal end portion of the insertion section. High-frequency current is supplied to the cutting wire to effect excision of an affected part of a patient. This type of endoscopic treatment instrument is disclosed in, e.g. Jpn. Pat. Appln. KOKAI Publication No. 5-176940 and Jpn. Pat. Appln. KOKAI Publication No. 4-307055.

The treatment instrument disclosed in Jpn. Pat. Appln. KOKAI Publication No. 5-176940 is provided with an outer sheath through which the body of the treatment instrument is movably inserted. By axially moving the outer sheath relative to the body of the treatment instrument, the length of the cutting wire exposed to the outside of the outer sheath is varied.

In the treatment instrument disclosed in Jpn. Pat. Appln. KOKAI Publication No. 4-307055, the surface of the electrically conductive cutting wire exposed to the distal end of the insertion section is coated with electrically conductive Teflon.

Where an EST (endoscopic sphincterotomy), for example, is performed using a cutting wire, the following operation is carried out. A distal end portion of the insertion section of the endoscope, which was pre-inserted in the body of a patient, is situated near a papilla. Then, an insertion section of the endoscopic treatment instrument is inserted in the body via the treatment instrument insertion channel in the endoscope. A distal end portion of the insertion section of the treatment instrument is projected out of the endoscope from a forceps opening formed at the distal end of the treatment instrument insertion channel. Under endoscopic observation, the distal end portion of the insertion section of the treatment instrument is inserted in the bile duct beyond the papilla. In this state, high-frequency current is supplied to the cutting wire, and the papillary sphincter is high-frequency heated and cut by the cutting wire.

In the case where the EST is performed by means of the treatment instrument disclosed in Jpn. Pat. Appln. KOKAI Publication No. 5-176940, if the endoscope body or a tissue near the papilla is in contact with the cutting wire, it is necessary to move the outer sheath so as to prevent such contact while observing an endoscopic image. In this case, however, the outer sheath needs to be moved while the distal end portion of the tube of the treatment instrument body is inserted in the bile duct beyond the papilla. It is thus possible that the tube of the treatment instrument body may be removed from the bile duct or the papilla during the operation of moving the outer sheath.

On the other hand, where the part near the papilla has a peculiar shape, for example, in the case of diverticulosisi the papilla is located deeper than the peripheral tissue. In such a case, it is difficult to move the endoscope body closer to the papilla. In such a case of disease, it may be advantageous to use a treatment instrument with a long knife length, thereby to make the direction of extension of the bile duct coincide with the axis of the tube of the treatment instrument body and the direction of the knife. With the treatment instrument according to Jpn. Pat. Appln. KOKAI Publication No. 5-176940, however, there is a concern that a tissue near the papilla, which is not a region-of-interest, may be damaged by a proximal-side portion of the cutting wire. Moreover, in this state, since the cutting wire is in contact with many body tissues, the density of electric current at the region-of-interest decreases and the excision of the papilla becomes difficult.

The treatment instrument according to Jpn. Pat. Appln. KOKAI Publication No. 5-176940 includes means for controlling the direction and shape of the distal end portion of the tube of the treatment instrument body by using an operating wire. It is very difficult, however, to perform at the same time the works for operating the outer sheath, the cutting wire, and the wire for changing the direction and shape of the distal end portion of the tube of the treatment instrument.

With the treatment instrument disclosed in Jpn. Pat. Appln. KOKAI Publication No. 4-307055, it is possible to prevent the cutting wire from adhering to the tissue in contact, but it is difficult to prevent the cutting wire from coming in contact with a body tissue which is not a region-of-interest.

BRIEF SUMMARY OF THE INVENTION

The present invention has been made in consideration of the above circumstances, and its object is to provide a treatment instrument for an endoscope which is capable of enhancing the safety and operability of an EST (endoscopic sphincterotomy).

In order to achieve the object, there is provided a treatment instrument for an endoscope which comprises: a main body, a cutting wire and an insertion portion. The cutting wire has an insertion portion inserted in the main body and an exposed portion situated at a distal side of the insertion portion and exposed out of the main body. The cutting wire is supplied with high-frequency current, and the insulating member electrically insulates a peripheral surface of the cutting wire. The insulates member insulating that part of the exposed portion, which is other than a non-insulated portion extending in a range of 5 mm to 15 mm from a distal end of the exposed portion. And the excision portion is formed of the non-insulated portion of the cutting wire.

In the present invention, only that portion of the exposed portion of the cutting wire, which is in the range of 5 mm to 15 mm from the front end of the exposed portion, can be provided with the function of an excisable knife. In the EST, only the thickness portion of the papilla can be cut. In this case, no high-frequency current is supplied to the insulated portion of the exposed portion of the cutting wire, from which the excision portion is excluded, even if the insulated portion is put in contact with the body tissue. Thus, damage to other tissues around the papilla and to the endoscope can be prevented as much as possible. In addition, the length of the excision portion having the function of a knife is small, and the region of the living tissue, to which high-frequency current is applied, is small. Accordingly, the density in current increases and the excision can be exactly performed.

Therefore, according to the present invention, the safety and operability of the EST (endoscopic sphincterotomy) is enhanced.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE INVENTION

A first embodiment of the present invention will now be described with reference to FIGS. 1A to 5. An endoscopic treatment instrument 1 in this embodiment includes a long insertion section 3, which is inserted in the body through an endoscope 2 (see FIG. 5), and a proximal-side operating section 4 coupled to a proximal end portion of the insertion section 3.

Figure 2:
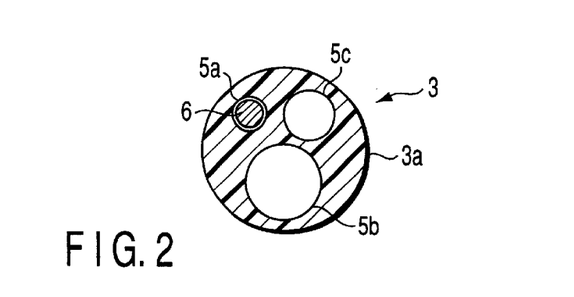
FIG. 2 is a transverse cross-sectional view of a tube of the insertion section of the endoscopic treatment instrument according to the first embodiment.

As is shown in FIG. 2, a main body 3a of the insertion section 3 of the treatment instrument 1 is formed of a single three-lumen tube having three lumens 5a, 5b and 5c. The three lumens in the three-lumen tube, i.e. a first lumen 5a, a second lumen 5b and a third lumen 5c, have different lumen diameters (inside diameters).

In this embodiment, a lumen diameter d1 of the first lumen 5a, a lumen diameter d2 of the second lumen 5b, and a lumen diameter d3 of the third lumen 5c have a relationship: $d1<d3<d2$. An electrically conductive cutting wire 6 (to be described later) is inserted in the first lumen 5a with the least lumen diameter. The main body 3a of the insertion section is not limited to the three-lumen tube, and may be a tube having at least one lumen 5.

Figure 1A:
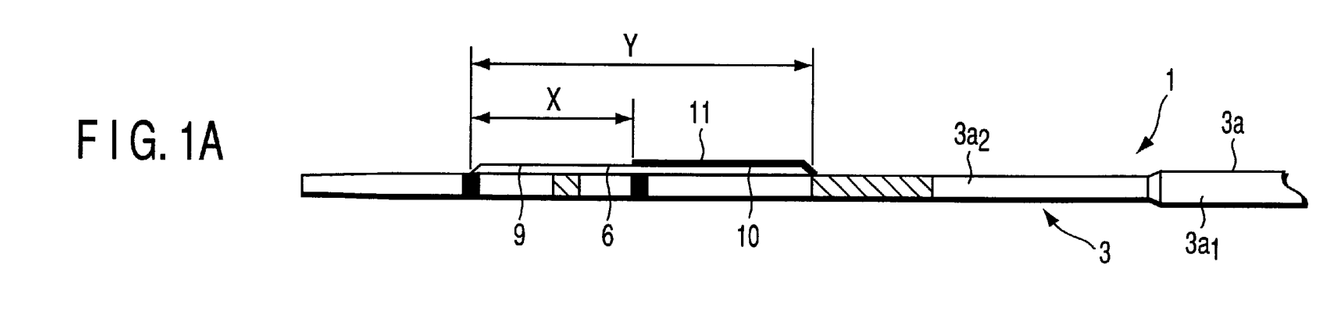
FIG. 1A is a side view showing a distal end portion of an insertion section of an endoscopic treatment instrument according to a first embodiment of the present invention.

As is shown in FIG. 1A, a distal end portion of the insertion section body 3a is provided with a small-diameter portion 3a2 which is less in diameter than a large-diameter portion 3a1. The outside diameter of the insertion section body 3a may be uniform over the entire length, or may vary with a tapering shape.

Figure 3:
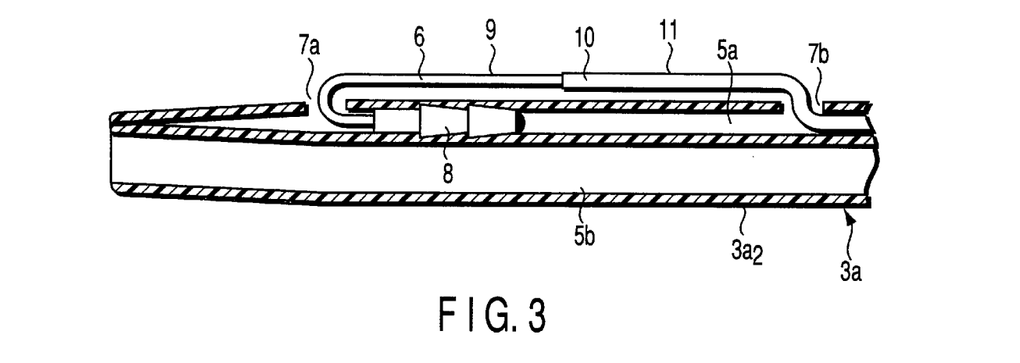
FIG. 3 is a longitudinal cross-sectional view of a main part of the invention, showing a distal end portion of the tube of the insertion section of the endoscopic treatment instrument according to the first embodiment.

A portion of the cutting wire 6 is exposed at a distal end portion of the small-diameter portion 3a2 of the insertion section body 3a. The distal end portion of the small-diameter portion 3a2 has two slits 7a and 7b which are spaced apart in a front-and-rear direction, as shown in FIG. 3. A distal end portion of the cutting wire 6 inserted in the first lumen 5a is exposed to the outside via the front and rear slits 7a and 7b. Thus, the portion of the cutting wire 6 between the front and rear slits 7a and 7b is exposed to the outside of the insertion section body 3a.

A knife tip 8 serving as an engaging member is connected to a distal end portion of the cutting wire 6. At the distal end portion of the cutting wire 6, the knife tip 8 is directed backward and fitted and fixed in the first lumen 5a via the front slit 7a. The position of fixation of the knife tip 8 is not limited to this.

As is shown in FIG. 1A, the exposed portion of the cutting wire 6, which has a length Y and is exposed at the distal end portion of the insertion section 3, includes a non-insulated excision portion 9 in a region X of 5 mm to 15 mm from the front end of the exposed portion. An insulated portion 10 is provided at the exposed portion of the cutting wire 6 from which the excision portion 9 is excluded.

The insulated portion 10 is formed by coating an outer periphery of a wire element of the cutting wire 6 with a fluororesin coating 11 of PFA (Perfluoroalkoxy) for insulation. The material of the coating 11 is not limited to this fluororesin. For example, one or two or more of the following resins may be used singly or in combination:

(a) PTFE (Polytetrafluoroethylene),
(b) Tetrafluoroethylene hexafluoropropylene (or FEP (Fluorinated ethylene propylene)),
(c) Tetrafluoroethylene-Perfluoroalkylvinylether copolymer,
(d) Polyimide,
(e) Polyethylene,
(f) Polyolefin,
(g) Polyamide,
(h) Vinyl chloride,
(i) Latex,
(j) Natural rubber,
(k) Polysulfone,
(l) Polyphenylsulfone,
(m) Polyether imide,
(n) Polyoxymethylene,
(o) Polyether ether ketone (PEEK),
(p) Polycarbonate, and
(q) Acrylonitrile-butadiene-styrene (ABS).

High-frequency current is supplied to the excision portion 9 of the exposed portion of the cutting wire 6, thereby to cut a living tissue of an affected part. The coating 11 may be colored in blue, white, green, etc. so as to make the coating 11 of insulated portion 10 distinguishable from the excision portion 9 of the exposed portion of the cutting wire 6.

A proximal end portion of the cutting wire 6 is extended to the operating section 4 through the first lumen 5a in the insertion section 3.

Figure 1B:
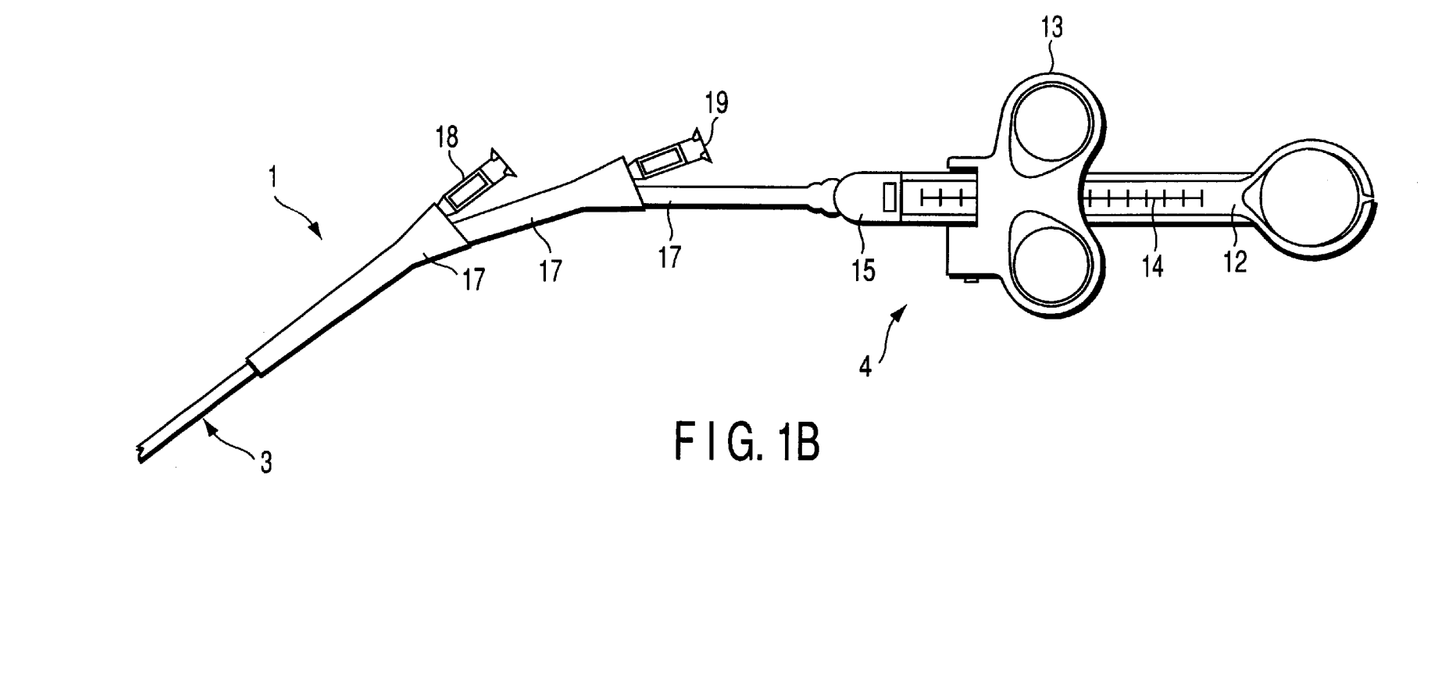
FIG. 1B is a side view showing an operating section of the endoscopic treatment instrument according to the first embodiment.

FIG. 1B shows the operating section 4 of the endoscopic treatment instrument 1 according to the embodiment. As is shown in FIG. 1B, the operating section 4 includes a rod-like main body 12 and a slider 13 which is axially slidable along the main body 12. A scale 14 for indicating the amount of movement of the slider 13 is provided on the main body 12 of operating section 4. The operator can confirm the amount of movement of the slider 13 while viewing the scale 14.

A proximal end portion of the cutting wire 6 is connected to the slider 13. When the slider 13 is pulled backward, the cutting wire 6 can be drawn.

Figure 4:
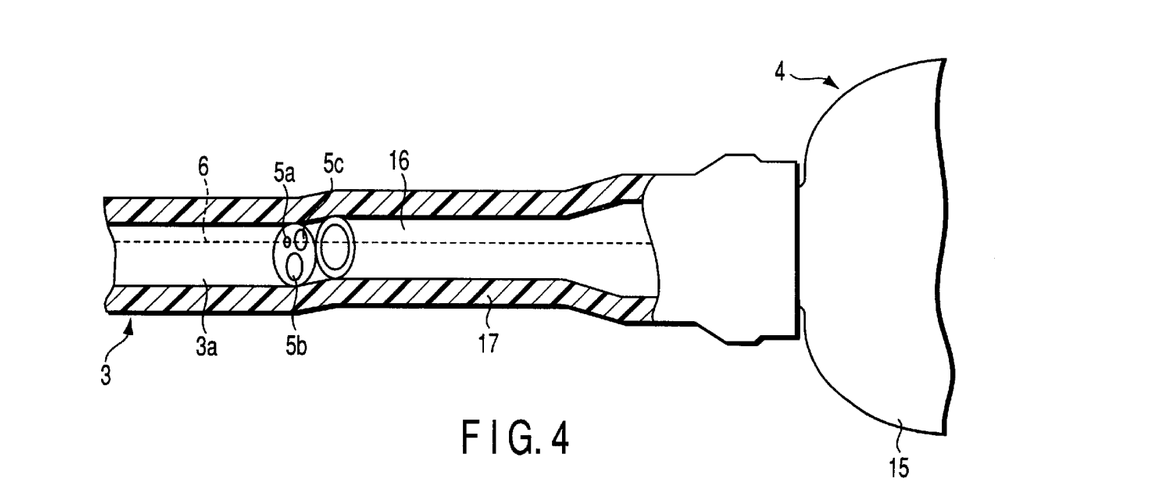
FIG. 4 is a view for describing a connection section between the tube of the insertion section of the endoscopic treatment instrument and the operating section according to the first embodiment.

FIG. 4 shows an example of a method of connecting the proximal end portion of the insertion section 3 and the operating section 4. A holder portion 15 is provided at an end portion of the operating section 4, which is coupled to the insertion section 3. A proximal end portion of a coupling tube 16 with a single lumen is fitted on the holder portion 15.

In addition, a heat-shrinkable tube 17 is provided at the coupling portion between the insertion section 3 and insertion section 4. As is shown in FIG. 4, in the state in which the proximal end portion of the main body 3a (three-lumen tube) of the insertion section 3 is abutted upon the distal end portion of the coupling tube 16, the proximal end portion of the main body 3a (three-lumen tube) of the insertion section 3 and the coupling tube 16 are inserted in the heat-shrinkable tube 17. Then, both are coupled by heat shrinkage of the heat-shrinkable tube 17. The heat-shrinkable tube 17 may be provided with an adhesive.

As is shown in FIG. 1B, a guide wire cock 18 and a liquid feed cock 19 are provided near the proximal portion of the insertion section 3, which is coupled to the operation section 4. The guide wire cock 18 is connected to the second lumen 5b, and the liquid feed cock 19 is connected to the third lumen 5c. These guide wire cock 18 and liquid feed cock 19 are coupled to the proximal end portion of the insertion section 3 by means of heat-shrinkage tubes 17.

On the outer peripheral surfaces of the guide wire cock 18 and liquid feed cock 19, characters or illustration may be indicated to make them distinguishable.

Figure 5:
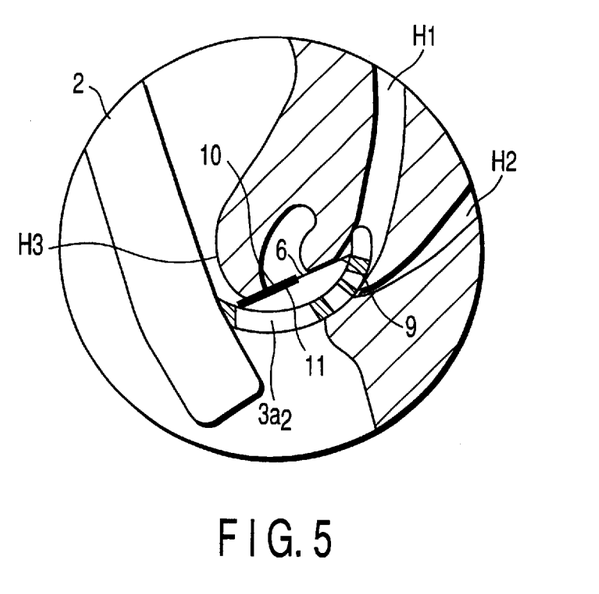
FIG. 5 is a view for describing how an EST is performed using the endoscopic treatment instrument according to the first embodiment.

The operation of the above structure will how be described. FIG. 5 is a view for describing how an EST (endoscopic sphincterotomy), for example, is performed using the endoscopic treatment instrument 1 according to this embodiment. In FIG. 5, H1 denotes a bile duct and H2 denotes a pancreatic duct.

When the EST is conducted, the following operation is performed. The distal end portion of the insertion section of the endoscope 2, which was pre-inserted in the body of a patient, is situated near a papilla H3. Then, the insertion section 3 of endoscopic treatment instrument 1 is inserted into the body through the treatment instrument insertion channel in the endoscope 2. The distal end portion of the insertion section 3 of the treatment instrument 1 is projected out of the endoscope 2 from the forceps opening formed at the distal end portion of the treatment instrument insertion channel in the endoscope 2. The distal end portion of the insertion section 3 of treatment instrument 1, which was projected outward, is inserted into the bile duct H1 beyond the papilla H3. In this state, high-frequency current is supplied to the excision portion 9 of cutting wire 6 alone, thereby cutting the papillary sphincter.

With the above construction, the following advantages are obtained. In this embodiment, the non-insulated excision portion 9 is provided in a range of 5 mm to 15 mm from the front end of the exposed portion of the cutting wire 6, which is exposed at the distal end portion of the insertion section 3 of endoscopic treatment instrument 1. The insulated portion 10 is provided at the other part of the exposed portion, from which the excision portion 9 is excluded. Thus, where the EST is conducted using the endoscopic treatment instrument 1, high-frequency current is supplied only to the excision portion 9 in the range X of 5 mm to 15 mm from the front end of the exposed portion with length Y of the cutting wire 6, which is exposed at the distal end portion of the insertion section 3. No high-frequency current is supplied to the insulated portion 10 of the exposed portion of cutting wire 6, from which the excision portion 9 is excluded. Accordingly, only that portion of the exposed portion of cutting wire 6, which is in the range X of 5 mm to 15 mm from the front end of the exposed portion, can be provided with the function of an excisable knife. In the EST, only the thickness portion of the papilla H3 can be cut, and damage to other tissues around the papilla and to the endoscope 2 can be prevented as much as possible. Even in a case where it is difficult to perform an EST with the conventional treatment instrument, the use of the treatment instrument 1 of this embodiment enables the EST to be carried out safely and exactly. Furthermore, the work of inserting the insertion section 3 of endoscopic treatment instrument 1 beyond the papilla is facilitated.

Since the length of the excision portion 9 with the knife function of the cutting wire 6 is small and the area put in contact with living tissues is decreased, the density in high-frequency current increases and the excision is exactly effected.

The end face of the coating 11 on the exposed portion of cutting wire 6 can be used as an index. By viewing the end face of the coating 11 under endoscopic observation, the depth of insertion of the cutting wire 6 of endoscopic treatment instrument 1 into the papilla H3 can be easily measured.

In most cases, the thickness of a papillary sphincter of a human being is about 10 mm. The function of a knife is sufficiently attained if the portion of about 5 mm to 15 mm from the front end of the exposed portion of the cutting wire 6 is used, even in consideration of the condition of actual use of the knife, for example, a large-scale excision in which a papilla is greatly cut in the diametrical direction of the duct or a small-scale excision in which a papilla is slightly cut in the diametrical direction of the opening. However, in the case of the EST, in order to make the direction of extension of the bile duct H1 coincide with the position (direction) of the cutting wire 6, the length of the exposed portion of the cutting wire 6, which is exposed out of the insertion section body 3a of treatment instrument 1, needs to be about 20 mm to 35 mm.

Where the length of the exposed portion of the cutting wire 6 is small, the curvature of the distal end portion of the insertion section body 3a increases if the cutting wire 6 is pulled and the distal end portion of insertion section body 3a is curved in an arc, as shown in FIG. 5. Consequently, the curved shape of the distal end portion does not match with the direction of extension of the bile duct H1. However, as the length of the exposed portion of cutting wire 6 increases, there is a higher possibility that the living tissue other than the region-of-interest on the proximal side of the cutting wire 6 may be damaged or the endoscope 2 may be damaged by contact. Moreover, in the state in which the proximal-side portion of the cutting wire 6 is in contact with the living tissue other than the region-of-interest, the density in high-frequency current at the region-of-interest decreases and the excision cannot exactly be carried out.

According to the endoscopic treatment instrument 1 having the above structure of the present embodiment, the aforementioned dangerous problems can be avoided and the EST can be carried out safely and surely. Even a doctor with little experience can carry out the EST safely.

Figure 6:
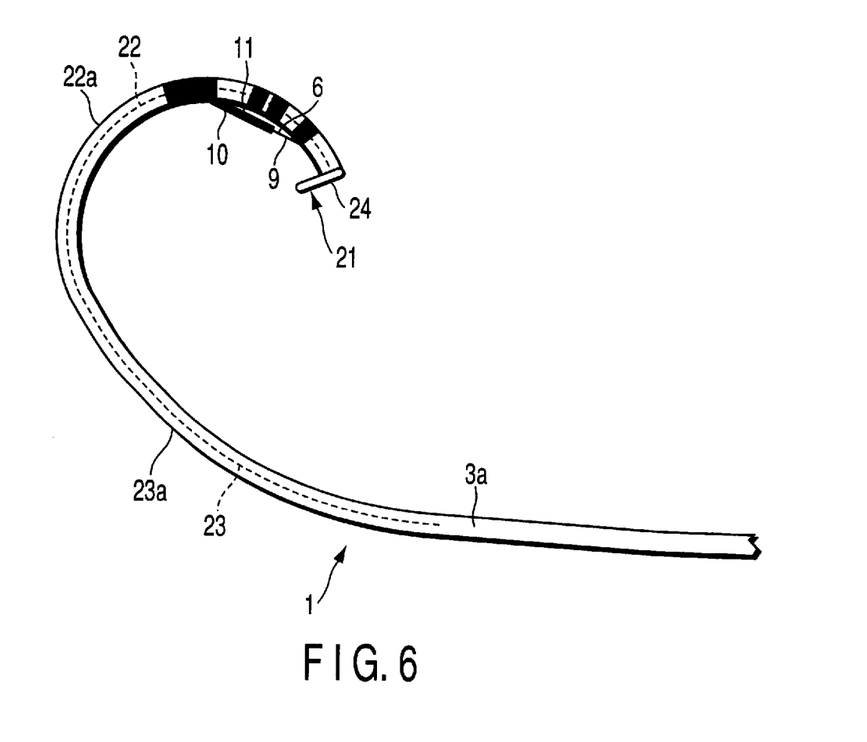
FIG. 6 is a side view showing an external appearance of a distal end portion of an insertion section of an endoscopic treatment instrument according to a second embodiment of the invention.
Figure 7:
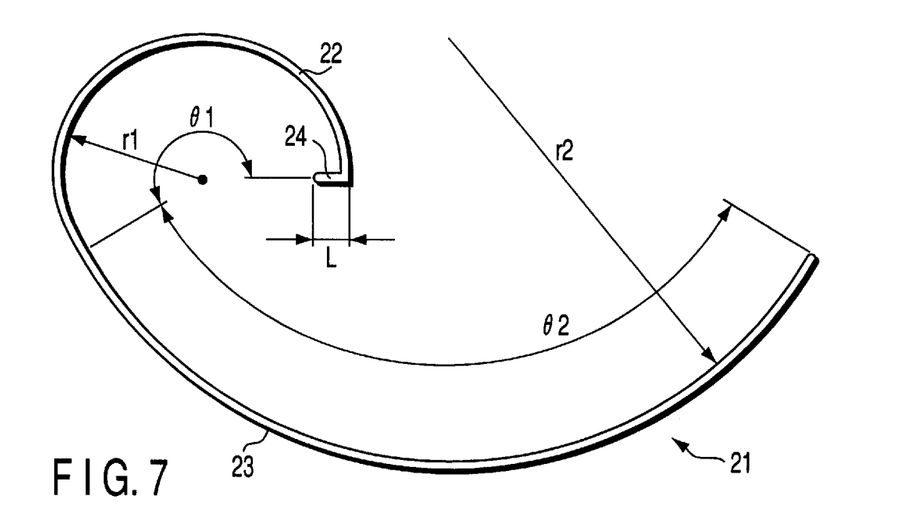
FIG. 7 is a side view showing a precurve stylet in the endoscopic treatment instrument according to the second embodiment.

A second embodiment of the present invention will now be described with reference to FIGS. 6 to 8C. In this embodiment, a wire-like precurve stylet 21 is provided. The precurve stylet 21 is used in combination with the endoscopic treatment instrument 1 according to the first embodiment (see FIGS. 1A, 1B and 5). The precurve stylet 21 is provided with curved (R) portions 22 and 23 with different radii of curvature, as shown in FIG. 7. One of the curved portions (first curved portion) 22, is provided on the distal side of the precurve stylet 21, and the other curved portion (second curved: portion) 23 is provided on the proximal side.

The first curved portion 22 has a radius r1 of, e.g. 20±5 mm and an opening angle θ1 of 210±20°. The second curved portion 23 has a radius r2 of, e.g. 60±10 mm and an opening angle θ2 of 210±20°.

A bent portion 24, which is bent substantially at right angles toward the inside of the curve, is provided at the distal end portion of the first curved portion 22 of the precurve stylet 21 according to this embodiment. The length L of the bent portion 24 is, e.g. about 5±1 mm. The difference (gap) between the outside diameter of the precurve stylet 21 and the inside diameter of the lumen 5 of the insertion section body 3a of endoscopic treatment instrument 1 in which the precurve stylet 21 is inserted is set at about 0.3 mm or less. The precurve stylet 21 in this embodiment is formed of a metallic material such as stainless steel or a resin material.

The operation of the above structure will now be described. When the endoscopic treatment instrument 1 of this embodiment is used, the precurve stylet 21 is inserted in the lumen 5 of insertion section body 3a for a predetermined time period, as shown in FIG. 6. In this case, since the precurve stylet 21 is inserted in the lumen 5 of insertion section body 3a of endoscopic treatment instrument 1 for a predetermined time period, curling portions corresponding to the shape of the precurve stylet 21 are provided on the insertion section body 3a of endoscopic treatment instrument 1. Specifically, two curling portions 22a and 23a corresponding to the shapes of the first curved portion 22 at the distal side of precurve stylet 21 and the second curved portion 23 at the proximal side of precurve stylet 21 are provided on the insertion section body 3a.

Figure 8A:
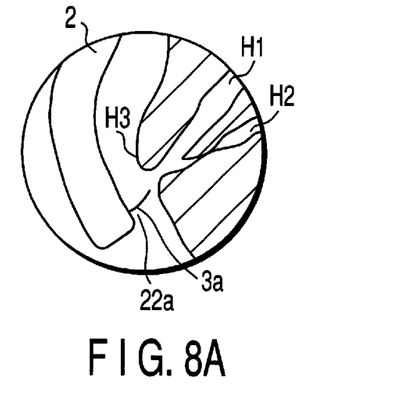
FIG. 8A is a view for describing a method of approaching the endoscopic treatment instrument according to the second embodiment to a papilla for an EST, the papilla having a shape as in a general case of disease.
Figure 8B:
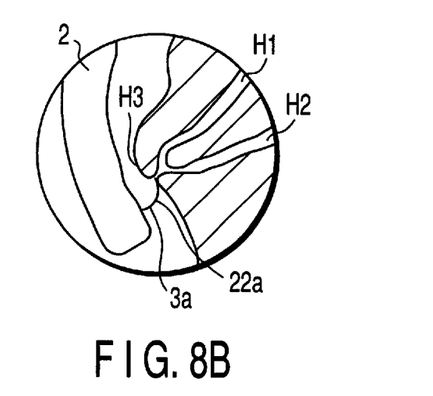
FIG. 8B is a view for describing a method of approaching the endoscopic treatment instrument according to the second embodiment to a papilla for an EST, the papilla having a downwardly bending upper portion.
Figure 8C:
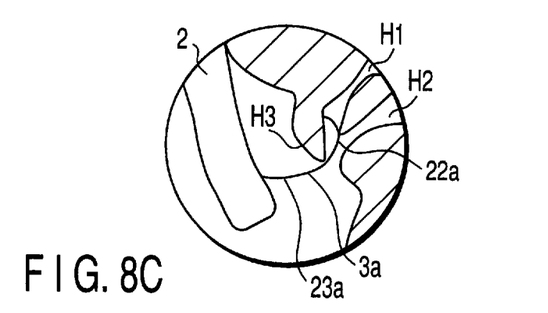
FIG. 8C is a view for describing a method of approaching the endoscopic treatment instrument according to the second embodiment to a papilla for an EST, in such a case as diverticulosis where a scope is not accessible to the papilla.

As has been described above, in this embodiment, the insertion section body 3a of endoscopic treatment instrument 1 can be provided with two different curling portions 22a and 23a. Thus, if the length of the insertion section body 3a of endoscopic treatment instrument 1, which is projected from the distal end of the endoscope 2, is adjusted as shown in FIGS. 8A to 8C, the direction of the distal end portion of insertion section body 3a of endoscopic treatment instrument 1 and the shape of insertion section body 3a of endoscopic treatment instrument 1 can be variously adjusted. Accordingly, the insertion section body 3a of endoscopic treatment instrument 1 can be easily suited to various shapes of papillary openings and bile ducts.

FIGS. 8A to 8C show states in which the EST is carried out using the endoscopic treatment instrument 1 according to the present embodiment, with the precurve stylet 5 removed from the insertion section 3.

FIG. 8A illustrates a method of approaching the insertion section body 3a of endoscopic treatment instrument 1 to the papilla H3 having a shape as in a general case of disease.

FIG. 8B illustrates a method of approaching the insertion section body 3a of endoscopic treatment instrument 1 to the papilla H3 having a downwardly bending upper portion. FIG. 8C illustrates a method of approaching the insertion section body 3a of endoscopic treatment instrument 1 to the papilla H3, in such a case as diverticulosis where the endoscope 2 is not accessible to the papilla H3.

In the above structure, without the need to perform a special process such as a heat process, the insertion section body 3a of endoscopic treatment instrument 1 can easily be provided with the two curling portions 22a and 23a corresponding to the shapes of the first curved portion 22 of the precurve stylet 21 and the second curved portion 23 on the proximal side. In addition, by virtue of the two curling portions 22a and 23a with different shapes, the angle and shape of the insertion section body 3a of endoscopic treatment instrument 1, which is projected out of the endoscope 2, can be adjusted. Accordingly, the insertion section body 3a of endoscopic treatment instrument 1 can be efficiently guided to the papilla H3 and bile duct H1 in various cases where it is difficult to approach the endoscope 2 and the insertion section body 3a of endoscopic treatment instrument 1, for example, a case where an upper portion of the papilla bends downward or a case where the endoscope 2 cannot be approached to the papilla H3 as in diverticulosis near the papilla.

The present invention is not limited to the above embodiments and, needless to say, various modifications may be made without departing from the spirit of the present invention.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A treatment instrument comprising:
    a main body adapted to be inserted into an endoscope channel;
    a cutting wire having an insertion portion inserted in said main body, and an exposed portion that is exposed outside said main body, said cutting wire being adapted to be supplied with high-frequency current; and
    an insulating member that covers a peripheral surface of a part of said exposed portion of said cutting wire,
    wherein said exposed portion of said cutting wire is substantially straight and comprises an insulated portion which is the part of said exposed portion of said cutting wire whose peripheral surface is covered by the insulating member, and a non-insulated portion which is not covered by the insulating member and which is preset to extend in a range of 5 mm to 15 mm from a distal end of the exposed portion of said cutting wire,
    wherein said non-insulated portion of said exposed portion of the cutting wire comprises an excision portion of said treatment instrument,
    wherein said main body is bendable, and
    wherein said substantially straight exposed portion of the cutting wire is exposed outside said main body through side ports provided in a side surface of a distal end portion of said main body, and said substantially straight exposed portion of the cutting wire extends adjacent to the side surface of the distal end portion of the main body between the side ports in a longitudinal direction of said main body.

2. A treatment instrument according to claim 1, wherein said insulating member comprises a coating portion formed of a highly insulative material.

3. A treatment instrument according to claim 1, wherein said insulating member comprises at least one of the following resins:
    (a) PTFE (Polytetrafluoroethylene),
    (b) Tetrafluoroethylene hexafluoropropylene (or FEP (Fluorinated ethylene propylene)),
    (c) Tetrafluoroethylene-Perfluoroalkylvinylether copolymer,
    (d) Polyimide,
    (e) Polyethylene,
    (f) Polyolefin,
    (g) Polyamide,
    (h) Vinyl chloride,
    (i) Latex,
    (j) Natural rubber,
    (k) Polysulfone,
    (l) Polyphenylsulfone,
    (m) Polyether imide,
    (n) Polyoxymethylene,
    (o) Polyether ether ketone (PEEK),
    (p) Polycarbonate, and
    (q) Acrylonitrile-butadiene-styrene (ABS).

4. A treatment instrument according to claim 1, wherein said insulating member is colored so as to be easily distinguishable from said cutting wire.

5. A treatment instrument according to claim 4, wherein said insulating member is different in color from said cutting wire so as to have enhanced visibility.

6. A treatment instrument according to claim 1, wherein said insulating member is colored so as to be easily distinguishable from living tissue in a body cavity.

7. A treatment instrument according to claim 6, wherein said insulating member is different in color from the living tissue in said body cavity so as to have enhanced visibility.

8. A treatment instrument according to claim 1, wherein said insulating member comprises a heatshrinkable tube.

9. A treatment instrument according to claim 1, wherein said insulating member has an outside diameter that is equal to or substantially equal to an outside diameter of said cutting wire.

10. A treatment instrument according to claim 1, wherein said cutting wire is adapted to be used for an operation excision of a duodenum papillary sphincter.

11. A treatment instrument comprising:
    a tube adapted to be inserted in an endoscope channel;
    a cutting wire having an insertion portion inserted in said tube, and an exposed portion that is exposed outside the tube, said cutting wire being adapted to be supplied with high-frequency current; and
    an insulating member that covers a peripheral surface of a part of said exposed portion of said cutting wire,
    wherein said exposed portion of said cutting wire is substantially straight and comprises an insulated portion which is the part of said exposed portion of said cutting wire whose peripheral surface is covered by the insulating member, and a non-insulated portion which is not covered by the insulating member and which is preset to extend in a range of 5 mm to 15 mm from a distal end of the exposed portion of said cutting wire,
    wherein said non-insulated portion of said exposed portion of the cutting wire comprises an excision portion of said treatment instrument, wherein tube is bendable, and wherein said substantially straight exposed portion of the cutting wire is exposed outside said tube through side ports provided in a side surface of a distal end portion of said tube, and said substantially straight exposed portion of the cutting wire extends adjacent to the side surface of the distal end portion of the tube between the side ports in a longitudinal direction of said tube.

12. A treatment instrument for an endoscope, comprising:

a tube member;

a cutting wire having an exposed portion provided on a side of said tube member; and an insulating member that covers an outer periphery of a part of said exposed portion of said cutting wire, wherein said exposed portion of said cutting wire is substantially straight and comprises an insulated portion which is the part of said exposed portion of said cutting wire whose peripheral surface is covered by the insulating member, and a non-insulated portion which is not covered by the insulating member and which is preset to extend along said tube member in a range of 5 mm to 15 mm from a distal end of said cutting wire, wherein tube member is bendable, and wherein said substantially straight exposed portion of the cutting wire is exposed outside said tube member through side ports provided in a side surface of a distal end portion of said tube member, and said substantially straight exposed portion of the cutting wire extends adjacent to the side surface of the distal end portion of the tube member between the side ports in a longitudinal direction of said tube member.

13. A treatment instrument according to claim 12, wherein said exposed portion has a length sufficient to be able to perform at least an excision operation.

14. A treatment instrument comprising:

a main body having a distal end, a proximal end, and central axis, said main body being bendable and adapted to be inserted into an endoscope channel;

a cutting wire having an insertion portion inserted in said main body, and a substantially straight exposed portion that is situated at a distal side of said main body and that extends substantially parallel to said central axis of the main body at one side thereof, said cutting wire being adapted to be supplied with high-frequency current; and an index provided on the exposed portion of said cutting wire that indicates an excision portion of the cutting wire that is preset to 5 to 15 mm from a distal end of the cutting wire, wherein said substantially straight exposed portion of the cutting wire is exposed outside said main body through side ports provided in a side surface of a distal end portion of said main body, and said substantially straight exposed portion of the cutting wire extends adjacent to the side surface of the distal end portion of the main body between the side ports in a longitudinal direction of said main body.

15. The treatment instrument according to claim 14, wherein said index comprises a sheath covering the cutting wire.

16. The treatment instrument according to claim 15, wherein said sheath is formed of an insulating material.

* * * * *